(12) United States Patent
Kim et al.

(10) Patent No.: US 10,806,800 B2
(45) Date of Patent: Oct. 20, 2020

(54) PHARMACEUTICAL COMPOSITION CONTAINING HYALURONIC ACID NANOPARTICLES FOR PREVENTING OR TREATING INFLAMMATORY DISEASE AND METABOLIC DISEASE

(71) Applicant: AJOU UNIVERSITY INDUSTRY-ACADEMIC COOPERATION FOUNDATION, Suwon-si, Gyeonggi-do (KR)

(72) Inventors: Wook Kim, Suwon-si (KR); Hwa Seung Han, Suwon-si (KR); Jae Hyung Park, Suwon-si (KR); Jun Gi Rho, Ansan-si (KR); Juhwan Yoon, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/340,897

(22) PCT Filed: Sep. 28, 2017

(86) PCT No.: PCT/KR2017/010824
§ 371 (c)(1),
(2) Date: Apr. 10, 2019

(87) PCT Pub. No.: WO2018/070711
PCT Pub. Date: Apr. 19, 2018

(65) Prior Publication Data
US 2019/0231898 A1      Aug. 1, 2019

(30) Foreign Application Priority Data

Oct. 11, 2016   (KR) .......................... 10-2016-0131347

(51) Int. Cl.
| | | |
|---|---|---|
| *A61K 47/54* | (2017.01) | |
| *A61K 47/69* | (2017.01) | |
| *A61P 3/04* | (2006.01) | |
| *A61P 3/10* | (2006.01) | |
| *A61P 29/00* | (2006.01) | |
| *A61P 19/02* | (2006.01) | |
| *A61K 47/59* | (2017.01) | |
| *A61K 9/00* | (2006.01) | |
| *A23L 33/10* | (2016.01) | |
| *A61K 31/728* | (2006.01) | |
| *A61K 47/34* | (2017.01) | |
| *A23L 33/00* | (2016.01) | |

(52) U.S. Cl.
CPC .......... *A61K 47/6925* (2017.08); *A23L 33/00* (2016.08); *A23L 33/10* (2016.08); *A61K 9/0056* (2013.01); *A61K 31/728* (2013.01); *A61K 47/34* (2013.01); *A61K 47/54* (2017.08); *A61K 47/593* (2017.08); *A61P 3/04* (2018.01); *A61P 3/10* (2018.01); *A61P 19/02* (2018.01); *A61P 29/00* (2018.01); *A23V 2002/00* (2013.01)

(58) Field of Classification Search
CPC .......... A61P 3/10; A61P 19/02; A61K 47/554; A61K 47/6939; A23V 2250/51; A23V 220/25; A23V 2200/324
See application file for complete search history.

(56) References Cited

FOREIGN PATENT DOCUMENTS

| KR | 10-2011-0032561 A | 3/2011 |
|---|---|---|
| WO | 2016/011436 A1 | 1/2016 |

OTHER PUBLICATIONS

Mayo clinic; title: Type 1 diabetes in children; downloaded from https://www.mayoclinic.org/diseases-conditions/type-1-diabetes-in-children/symptoms-causes/syc-20355306?page=0&citems=10, Feb. 25, 2020. (Year: 2020).*
Mayo clinic; title: Rheumatoid arthritis; downloaded from https://www.mayoclinic.org/diseases-conditions/rheumatoid-arthritis/symptoms-causes/syc-20353648?p=1, Feb. 25, 2020. (Year: 2020).*
Kang, et al; title: CD44 Plays a Critical Role in Regulating Diet-Induced Adipose Inflammation, Hepatic Steatosis, and Insulin Resistance; PLOS one, vol. 8, issue 3, published Mar. 7, 2013. (Year: 2013).*
Ga Young Lee et al., "Hyaluronic acid nanoparticles for active targeting atherosclerosis", Biomaterials, 2015, vol. 53, pp. 341-348.
Ki Young Choi et al., "Self-assembled hyaluronic acid nanoparticles as a potential drug carrier for cancer therapy: synthesis, characterization, and in vivo biodistribution", Journal of Materials Chemistry, 2009, vol. 19, pp. 4102-4107.
Kayo Masuko et al., "Anti-inflammatory effects of hyaluronan in arthritis therapy: Not just for viscosity", International Journal of General Medicine, 2009, pp. 77-81, vol. 2.
Eun Ji Shin et al., "Effects of Molecular Weights of Sodium Hyaluronate on the Collagen Synthesis, Anti-inflammation and Transdermal Absorption", J. Soc. Cosmet. Sci. Korea, Sep. 2016, vol. 42, No. 3, pp. 235-245.

(Continued)

*Primary Examiner* — Yanzhi Zhang
(74) *Attorney, Agent, or Firm* — Sughrue Mion, PLLC

(57) ABSTRACT

Disclosed is use of a composition for preventing or treating an inflammatory disease and a metabolic disease. The composition includes hyaluronic acid nanoparticles formed in such a way that 5β-cholanic acid or polycaprolactone binds to a hydrophobic moiety of hyaluronic acid through self-assembly in an aqueous solution state.

2 Claims, 8 Drawing Sheets
Specification includes a Sequence Listing.

(56) References Cited

OTHER PUBLICATIONS

S. M. Ruppert et al., "Tissue integrity signals communicated by high-molecular weight hyaluronan and the resolution of inflammation", Immunologic Research, Mar. 11, 2014, vol. 58, pp. 186-192.
Ki Young Choi et al., "Hyaluronic acid-based nanocarriers for intracellular targeting: Interfacial interactions with proteins in cancer", Colloids and Surfaces B: Biointerfaces, 2012, vol. 99, pp. 82-94.
Korean Intellectual Property Office, Office Action for corresponding KR 10-2016-0131347, dated Aug. 9, 2017.
Korean Intellectual Property Office, Office Action for corresponding KR 10-2016-0131347, dated Mar. 29, 2018.
Korean Intellectual Property Office, Grant of Patent for corresponding KR 10-2016-0131347, dated Sep. 27, 2018.
International Search Report for PCT/KR2017/010824, dated Apr. 5, 2018.

\* cited by examiner

HACA

PHARMACEUTICAL COMPOSITION CONTAINING HYALURONIC ACID NANOPARTICLES FOR PREVENTING OR TREATING INFLAMMATORY DISEASE AND METABOLIC DISEASE

CROSS REFERENCE TO RELATED APPLICATIONS

This Application is a National Stage of Application No. PCT/KR2017/010824 filed Sep. 28, 2017, claiming priority based on Korean Patent Application No. 10-2016-0131347 filed Oct. 11, 2016.

TECHNICAL FIELD

The present invention relates to a pharmaceutical composition for preventing or treating an inflammatory disease or a metabolic disease, which includes hyaluronic acid nanoparticles, and more particularly, to a pharmaceutical composition for preventing or treating an inflammatory disease or a metabolic disease, which includes hyaluronic acid nanoparticles formed in such a way that 5β-cholanic acid or polycaprolactone binds to a hydrophobic moiety of hyaluronic acid through self-assembly in an aqueous solution state.

BACKGROUND ART

Hyaluronic acid (HA) is a linear polysaccharide polymer having a molecular weight ranging from $1 \times 10^5$ Da to $1 \times 10^7$ Da and is composed of repeating units of (β, 1-4)-D-glucuronic acid (GlcUA) and β, 1-3)-N-acetyl-D-glucosamine (GlcNAc). Hyaluronic acid is found in the extracellular matrix and cell surface of most human tissues, and especially is present in synovial fluid, cartilage, and the like in large amounts. Thus, hyaluronic acid has biocompatibility and is biodegraded by hyaluronidase, which is a hyaluronic acid enzyme present in blood, and thus is used as a biomaterial such as a drug carrier, a tissue engineering scaffold, or the like. In particular, hyaluronic acid is internalized through endocytosis by binding to CD44 and RHAMM, which are overexpressed on surfaces of cancer cells or metastatic cancer cells, and is degraded in a low pH environment such as lysosomes.

According to the International Diabetes Federation's report in 2015, as of 2014, there were approximately 380 million patients with diabetes worldwide. That is, diabetes is a typical metabolic syndrome, the incidence rate of diabetes continues to increase, and it is known that diabetes is accompanied by complications such as cardiovascular disease, stroke, chronic heart failure, and the like. Also in Korea, there are about 3 million diabetic patients and it is expected that there will be about 6 million diabetic patients in 2050. In particular, diabetes is one of the causes of death, other than cancer, heart disease, and brain diseases, and social/economic costs are increasing rapidly in proportion to the number of patients, and thus it is becoming a major social problem. Currently, there are commercially available anti-diabetic agents such as metformin, sulfonylurea, DPP-4 inhibitors, GLP-1 receptor analogs, and the like, but most thereof have low efficacy or some side effects such as hypoglycemic shock and liver toxicity, and thus these agents are limited in effectively treating diabetes. Recently, it has been reported that CD44 receptors are closely related to the progression and treatment of diabetes (Kodama et al., Diabetes, 64(3), 2015, 867-875), and based on this, hyaluronic acid-based nanoparticles specifically binding to these CD44 receptors have been developed under determination that inflammatory diseases and metabolic diseases can be prevented or treated by blocking CD44 receptors using hyaluronic acid-based nanoparticles.

Therefore, as a result of having prepared hyaluronic acid nanoparticles including hyaluronic acid and 5β-cholanic acid or polycaprolactone and having made efforts to verify effects thereof, the inventors of the present invention confirmed that the hyaluronic acid nanoparticles reduced body weight, lowered food intake, had an effect of reducing blood glucose as a result of a glucose tolerance test (GTT), and had an effect of reducing insulin resistance, inflammatory inducers (NF-κB, IL-1β, CD44, TNF-α, NLRP3 inflammasome, and the like), and macrophage tissue infiltration, thus completing the present invention.

DISCLOSURE

Technical Problem

Therefore, the present invention has been made in view of the above problems, and it is an object of the present invention to provide a pharmaceutical composition for preventing or treating an inflammatory disease or a metabolic disease, which includes hyaluronic acid nanoparticles.

It is another object of the present invention to provide a food for alleviating an inflammatory disease or a metabolic disease, which includes hyaluronic acid nanoparticles.

Technical Solution

In accordance with the present invention, the above and other objects can be accomplished by the provision of a pharmaceutical composition for preventing or treating an inflammatory disease or a metabolic disease, which includes hyaluronic acid nanoparticles represented by Formula (1) or (2) below:

[Formula 1]

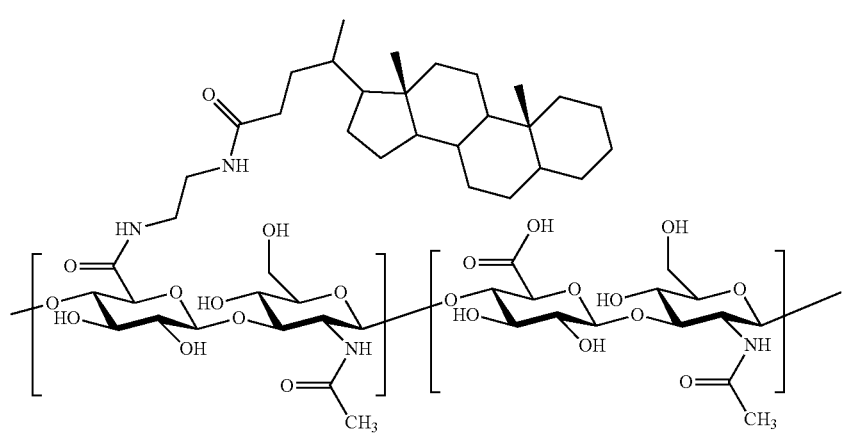

[Formula 2]

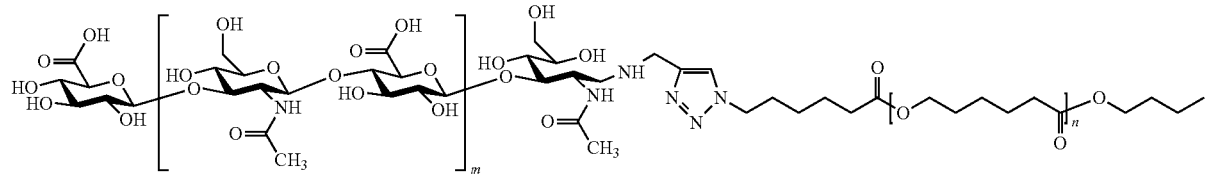

In accordance with an aspect of the present invention, the above and other objects can be accomplished by the provision of a food for alleviating an inflammatory disease or a metabolic disease, which includes hyaluronic acid nanoparticles represented by Formula (1) or (2).

DESCRIPTION OF DRAWINGS

The above and other objects, features and other advantages of the present invention will be more clearly understood from the following detailed description taken in conjunction with the accompanying drawings, in which.

BEST MODE

Figure 1:
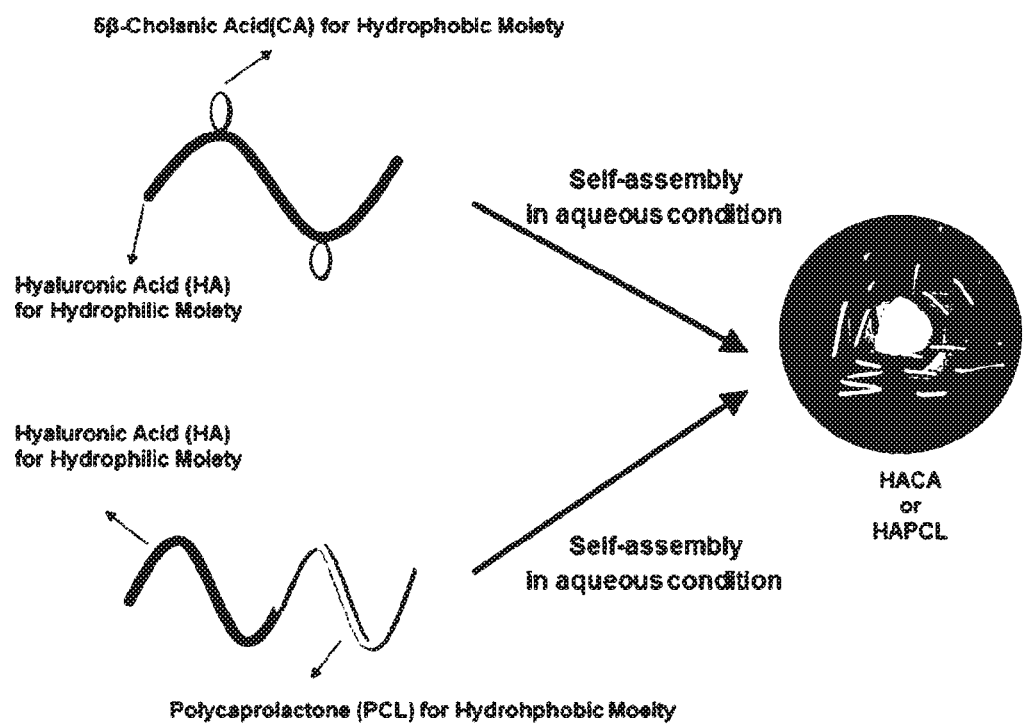
FIG. 1 illustrates hyaluronic acid nanoparticles according to an embodiment.

The present invention may be achieved by the following description. It is to be understood that exemplary embodiments are provided for illustrative purposes only, and these embodiments are not intended to limit the scope of the present invention. In addition, the accompanied drawings are provided for understanding of the present invention and are not intended to limit the present invention, and details of individual configurations may be properly understood by specific purposes of the following related descriptions.

Unless defined otherwise, technical and scientific terms used herein have the same meaning as is commonly understood by one of ordinary skill in the art to which the present invention pertains. Generally, the nomenclature used herein is well known in the art and commonly used.

In the present invention, hyaluronic acid nanoparticles including hyaluronic acid (HA) and 5β-cholanic acid (CA) or polycaprolactone (PCL) were prepared, and it was confirmed that the hyaluronic acid nanoparticles reduced body weight, lowered food intake, had an effect of reducing blood glucose as a result of a glucose tolerance test (GTT), and had an effect of reducing insulin resistance, inflammatory inducers (NF-κB, IL-1β, CD44, TNF-α, NLRP3 inflammasome, and the like), and macrophage tissue infiltration, and thus the hyaluronic acid nanoparticles may be effectively used as a pharmaceutical composition for preventing or treating an inflammatory disease or a metabolic disease.

Therefore, an embodiment of the present invention relates to a pharmaceutical composition for preventing or treating an inflammatory disease or a metabolic disease, which includes hyaluronic acid nanoparticles represented by Formula (1) or (2) below.

[Formula 1]

-continued

[Formula 2]

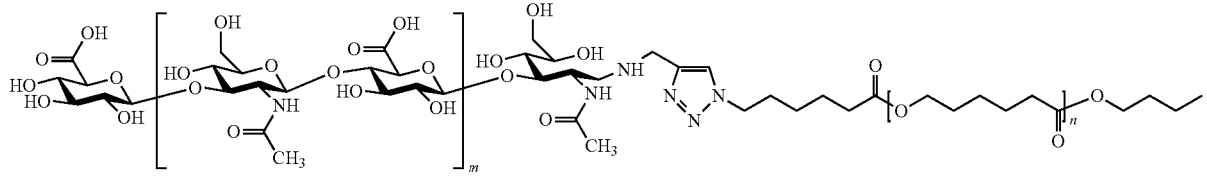

In the present invention, the hyaluronic acid nanoparticles of Formula (1) may consist of hyaluronic acid and 5β-cholanic acid, and the hyaluronic acid nanoparticles of Formula (2) may consist of hyaluronic acid and polycaprolactone.

In addition, the hyaluronic acid nanoparticles of Formula (1) of the present invention may consist of hyaluronic acid and 5β-cholanic acid in a mass ratio of 1:0.05 to 1:0.30, and the hyaluronic acid nanoparticles of Formula (2) may consist of hyaluronic acid and polycaprolactone in a mass ratio of 1:0.20 to 1:0.40.

In the present invention, as the hyaluronic acid nanoparticles, a hyaluronic acid conjugate of the hyaluronic acid nanoparticles of Formula (1) and (2) may be formed through self-assembly in an aqueous solution state.

In the hyaluronic acid conjugate constituting the hyaluronic acid nanoparticles of the present invention, the number average molecular weight of hyaluronic acid in the case of Formula (1) preferably ranges from 180,000 Da to 300,000 Da, more preferably from 200,000 Da to 250,000 Da, and the number average molecular weight of hyaluronic acid in the case of Formula (2) preferably ranges from 10,000 Da to 15,000 Da, more preferably from 11,000 Da to 13,000 Da. In addition, the size of the hyaluronic acid nanoparticles may range from 200 nm to 250 nm, and is most preferably 220 nm. When the number average molecular weight of hyaluronic acid of the hyaluronic acid conjugate constituting the hyaluronic acid nanoparticles is less than 5,000, the hyaluronic acid nanoparticles have a reduced ability to bind to CD44 and RHAMM, which are overexpressed on surfaces of metastatic cancer cells, and thus internalization of the nanoparticles is deteriorated, and when the size of the hyaluronic acid nanoparticles is 500 nm or larger, an EPR effect is deteriorated according to a decrease in residence time.

In the present invention, the pharmaceutical composition is effective in preventing or treating an inflammatory disease and a metabolic disease, and the inflammatory disease and the metabolic disease may be selected from the group consisting of type 1 diabetes, type 2 diabetes, hypertension, hyperlipidemia, obesity, coronary arteriosclerosis, arteriosclerosis, arthritis, pancreatitis, hepatitis, dermatitis, and degenerative nerve inflammation, but the present invention is not limited thereto. The pharmaceutical composition of the present invention is especially effective in treating diabetes, arthritis, or obesity.

It is known that CD44 receptors are overexpressed in the above-described inflammatory diseases, and it has recently been reported that the progression of inflammation may be inhibited by intracellular injection of CD44 antibodies capable of specifically binding to these CD44 receptors. Therefore, the hyaluronic acid nanoparticles of the present invention may be used as a preparation capable of effectively inhibiting inflammation, e.g., the above-described inflammatory diseases, by specifically binding the hyaluronic acid nanoparticles to a CD44 receptor.

In addition, the pharmaceutical composition including the hyaluronic acid nanoparticles of the present invention may further include a suitable carrier, excipient or diluent according to a general method. Examples of the carrier, the excipient, and the diluent that may be included in the pharmaceutical composition including the hyaluronic acid nanoparticles include, but are not limited to, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

The pharmaceutical composition including the hyaluronic acid nanoparticles of the present invention may be formulated into any one preparation selected from the group consisting of powders, pills, granules, capsules, suspensions, solutions for internal use, emulsions, syrups, sterilized aqueous solutions, non-aqueous solutions, suspensions, and suppositories, according to a general method.

The pharmaceutical composition may be formulated using generally used diluents or excipients such as fillers, extenders, binders, wetting agents, disintegrating agents, surfactants, and the like. Solid preparations for oral administration include tablets, pills, powders, granules, capsules, and the like, and such solid preparations may be formulated by mixing the hyaluronic acid nanoparticles with at least one excipient, e.g., starch, calcium carbonate, sucrose, lactose, gelatin, and the like. In addition to simple excipients, lubricants such as magnesium stearate and talc may also be used. Examples of liquid preparations for oral administration include suspensions, solutions for internal use, emulsions, syrups, and the like, and these liquid preparations may include, in addition to simple commonly used diluents, such as water and liquid paraffin, various types of excipients, for example, a wetting agent, a sweetener, a flavoring agent, a preservative, and the like. Preparations for parenteral administration include a sterilized aqueous solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate. Examples of suppository bases include Witepsol, Macrogol, Tween 60, cacao butter, laurin, glycerogelatin, and the like.

The pharmaceutical composition of the present invention may be administered orally or parenterally (e.g., intravenously, subcutaneously, intraperitoneally, or topically) depending on the intended method, and a dose of the pharmaceutical composition may vary depending on the health condition, body weight, and age of a patient, gender, diet, excretion rate, the severity of a disease, drug form, administration time, administration route, and administration period, but may be appropriately selected by those of ordinary skill in the art. However, for the desired effect, the hyaluronic acid nanoparticles of the present invention may be administered at a dose of 0.1 mg/kg (body weight) to 30 mg/kg (body weight), 0.1 mg/kg (body weight) to 20 mg/kg (body weight), or 1 mg/kg (body weight) to 10 mg/kg (body weight) with respect to a daily dose of the active ingredient, and may be administered once or several times a day. The dose is not intended to limit the scope of the present invention in any way.

In addition, the pharmaceutical composition of the present invention may be used alone or in combination with methods such as surgery, radiation therapy, hormone therapy, chemotherapy, or biological response modifiers, to prevent or treat an inflammatory disease and a metabolic disease.

Another embodiment of the present invention relates to a food for alleviating an inflammatory disease or a metabolic disease, which includes hyaluronic acid nanoparticles represented by Formula (1) or (2) below:

noodles, ramen, spaghetti, macaroni, and the like), fruit juices, various drinks, cookies, taffy, dairy products (e.g., butter, cheese, and the like), edible vegetable oils, margarine, vegetable proteins, retort foods, frozen foods, various seasonings (e.g., soybean paste, soy sauce, other sauces, and the like), and the like.

The health functional food also includes various forms such as a functional food, a nutritional supplement, a health food, food additives, and the like as a food composition, and may be prepared in various forms according to a general method known in the art, for example, in the form of tea, juice, or drinks by using the above-described hyaluronic acid nanoparticles, in the form of granules, capsules, or powders, or by adding such a compound or extract to various foods such as beverages, fruits and processed foods thereof, fish, meat and processed foods thereof, bread, noodles, seasonings, and the like.

[Formula 1]

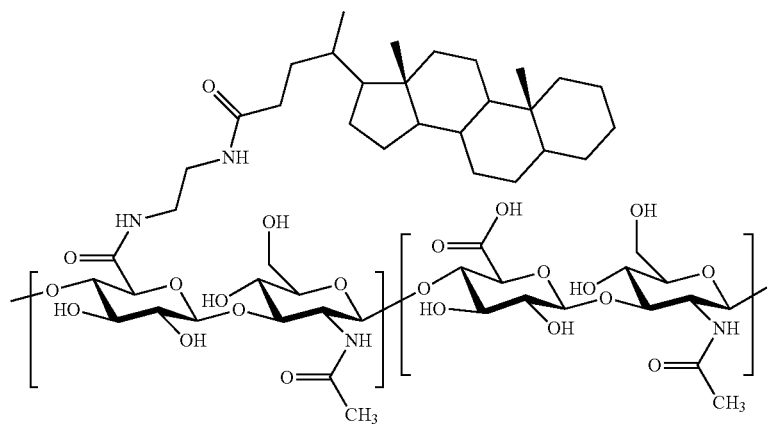

[Formula 2]

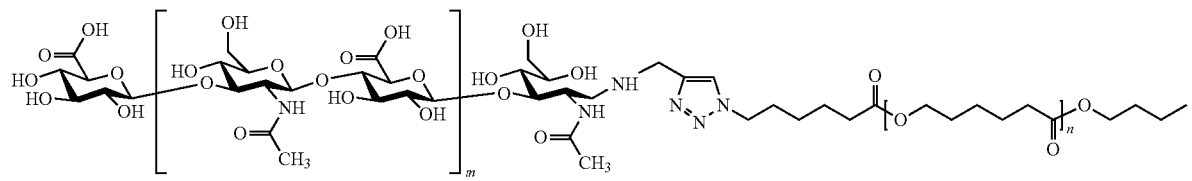

The inflammatory disease and the metabolic disease, symptoms of which may be alleviated by the food according to the present invention, are the same as described above. The food according to the present invention is effective in treating inflammatory and metabolic diseases, especially diabetes, arthritis, and obesity.

In the present invention, the food includes all forms such as a functional food, a nutritional supplement, a health food, food additives, and the like. The above type of health functional food may be prepared in various forms according to general methods known in the art. For example, as the health food, the hyaluronic acid nanoparticles of the present invention may be prepared in the form of teas, juices, and drinks, or may be granulated, capsulated, and powdered. In addition, functional foods may be prepared by adding the hyaluronic acid nanoparticles of the present invention to beverages (including alcoholic beverages), fruits and processed foods thereof (e.g., canned fruits, bottled foods, jam, marmalade, and the like), fish, meat and processed foods thereof (e.g., ham, sausage, corn, beef, and the like), bread and noodles (e.g., Japanese-style noodles, buckwheat The terms as used herein may be defined as follows.

The term "insulin resistance" as used herein refers to a reduced ability of insulin to reduce blood glucose such that cells are unable to effectively metabolize glucose. High insulin resistance causes the human body to produce too much insulin, resulting in the occurrence of hypertension or abnormal lipedema as well as heart disease, diabetes, and the like.

EXAMPLES

Hereinafter, the present invention will be described in further detail with reference to the following examples. It will be obvious to those of ordinary skill in the art that these examples are provided for illustrative purposes only and are not intended to limit the scope of the present invention.

Example 1: Preparation of Hyaluronic Acid Nanoparticles HA-CA 600 mg of hyaluronic acid was dissolved in 120 ml of formamide, 199 mg of aminoethyl-5-β-cholanoamide was dissolved in 200 ml of dimethylformamide, the resulting solutions were slowly added dropwise to a glycol hyaluronic acid solution, 364 mg of 1-ethyl-3-(3-dimethyl-aminopropyl)carbodiimide (EDC) and 219 mg of N-hydroxysuccinimide (NHS) were dissolved in 40 ml of dimethylformamide, the resulting solution was added to the reaction solution, and then the resulting reaction solution was stirred at room temperature for 24 hours. Subsequently, the reaction solution was dialyzed for 2 days to remove unreacted materials, and then lyophilized to obtain hyaluronic acid nanoparticles (HA-CA).

Figure 2:
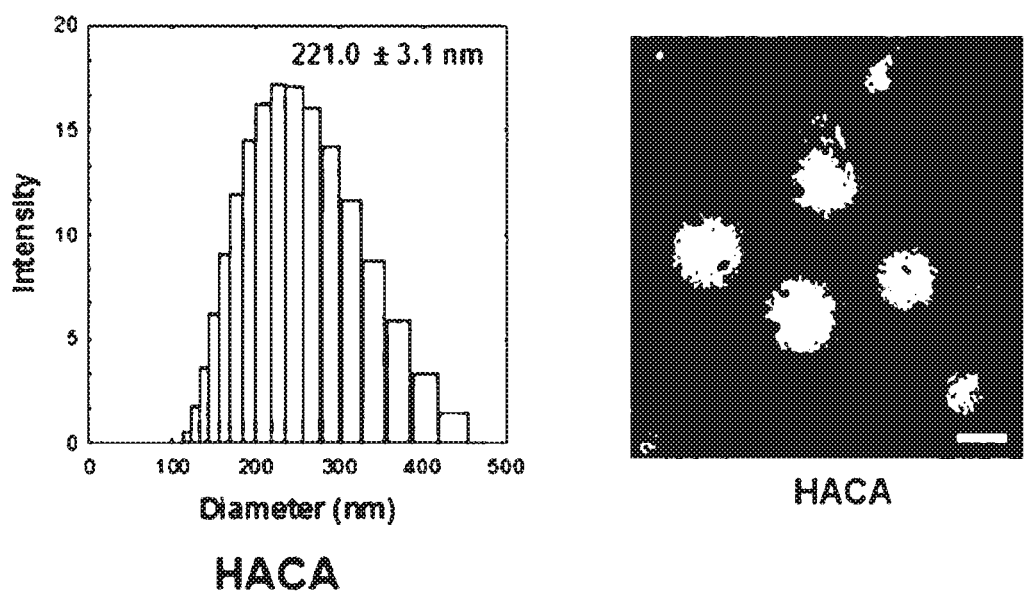
FIG. 2 illustrates the size and a TEM image of hyaluronic acid nanoparticles HA-CA according to an embodiment.

FIG. 2 illustrates the size and a TEM image of hyaluronic acid nanoparticles HA-CA, from which it was confirmed that the size was evenly distributed from 100 nm to 400 nm, and an average size was about 221±3.1 nm. It was also confirmed that, when dried hyaluronic acid nanoparticles HA-CA were dispersed in a PBS buffer, functional groups of 5β-cholanic acid agglomerated, thereby forming a spherical shape.

Example 2: Preparation of Hyaluronic Acid Nanoparticles HA-PCL 640 mg of hyaluronic acid and 290 mg of propargylamine were dissolved in a 0.1 M borate buffer solution including 0.4 M Sodium chloride solution and having a pH of 8.5, and then 330 mg of cyanoborohydride was slowly added dropwise to the resulting solution, followed by stirring at 50° C. for 5 days. Subsequently, the reaction solution was dialyzed for 3 days to remove unreacted materials, and then lyophilized to produce alkaline-modified hyaluronic acid. Click chemistry reaction between the alkaline-modified hyaluronic acid and azide-modified polycaprolactone proceeded under the following conditions. 200 mg of the alkaline-modified hyaluronic acid was dissolved in 40 ml of deionized water, 64 mg of the azide-modified polycaprolactone was dissolved in 40 ml of dimethylformamide, and the resulting solutions were mixed together. 10.60 mg of copper (II) sulfate pentahydrate and 8.41 mg of sodium ascorbate were added to the reaction solution, followed by stirring at 45° C. for 2 days. Thereafter, the reaction solution was dialyzed for 2 days to remove unreacted materials, and then lyophilized to obtain hyaluronic acid nanoparticles HA-PCL.

Figure 3:
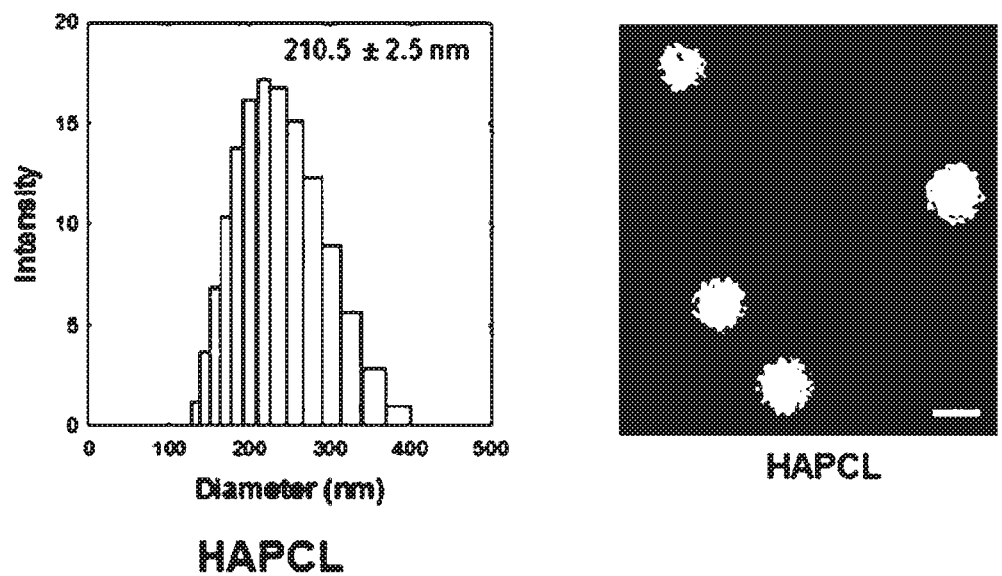
FIG. 3 illustrates the size and a TEM image of hyaluronic acid nanoparticles HA-PCL according to an embodiment.

FIG. 3 illustrates the size and a TEM image of hyaluronic acid nanoparticles HA-PCL, from which it was confirmed that the size was evenly distributed from 100 nm to 400 nm, and an average size was about 220±2.5 nm. It was also confirmed that, when dried hyaluronic acid nanoparticles HA-PCL were dispersed in PBS buffer, functional groups of polycaprolactone agglomerated, thereby forming a spherical shape.

Experimental Example 1: Effect of Hyaluronic Acid Nanoparticles on Metabolic Diseases (Obesity and Diabetes)

[Animal Experiments]

All animal experiments were performed in accordance with ethical guidelines for use of experimental animals of Ajou University.

4-week-old DBA/2 mice were used as obese/diabetic model mice and fed a 60% high fat diet for 5 months.

For the experiments, 20 mg/kg (body weight) of hyaluronic acid nanoparticles was injected into the tail vein of each mouse every day for about 30 days and sacrificed on the last day, and then blood, the liver, adipocytes, and the like of the mice were extracted.

[Hyaluronic Acid Nanoparticles]

The hyaluronic acid nanoparticles prepared according to Examples 1 and 2 were used in the all animal experiments (provided in a freeze-dried state from Sungkyunkwan University), and 8 mg to 10 mg of each of the hyaluronic acid nanoparticles HA-CA and HA-PCL was dissolved in 1 ml of a PBS buffer solution, and the hyaluronic acid nanoparticles were used at a concentration of 20 mg/kg.

1-1. Effect of Hyaluronic Acid Nanoparticles on Body Weight and Food Intake

200 µl/day of each of the hyaluronic acid nanoparticles HA-CA and HA-PCL was administered at a concentration of 20 mg/kg into diabetic model mice fed a high fat diet, for 4 weeks, and a PBS-administered group was used as a control.

Figure 4:
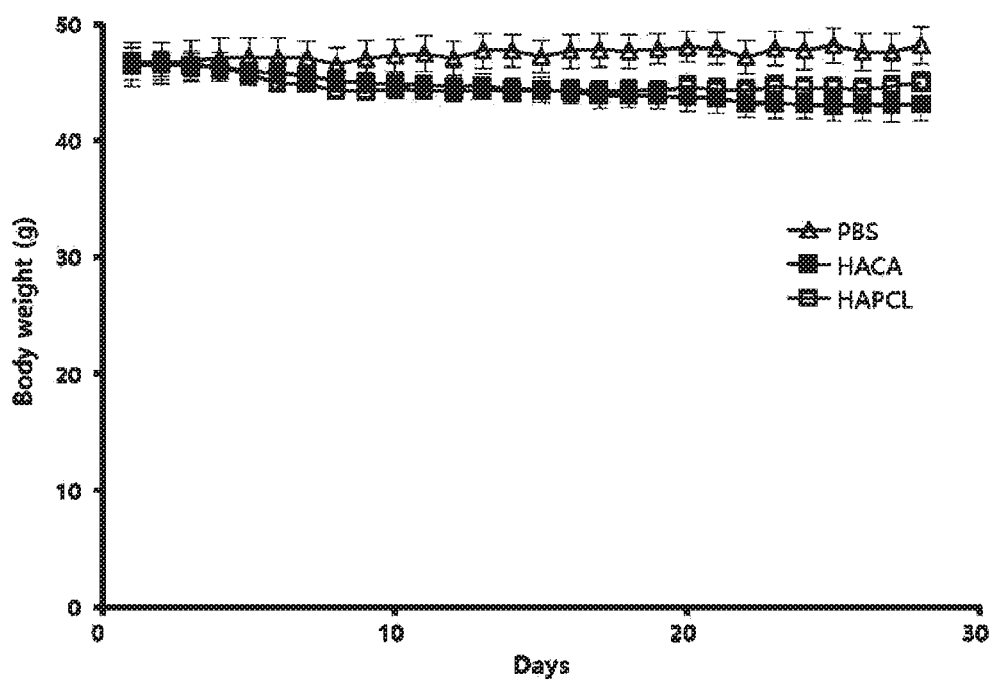
FIG. 4 illustrates the effect of hyaluronic acid nanoparticles according to an embodiment on body weight.
Figure 5:
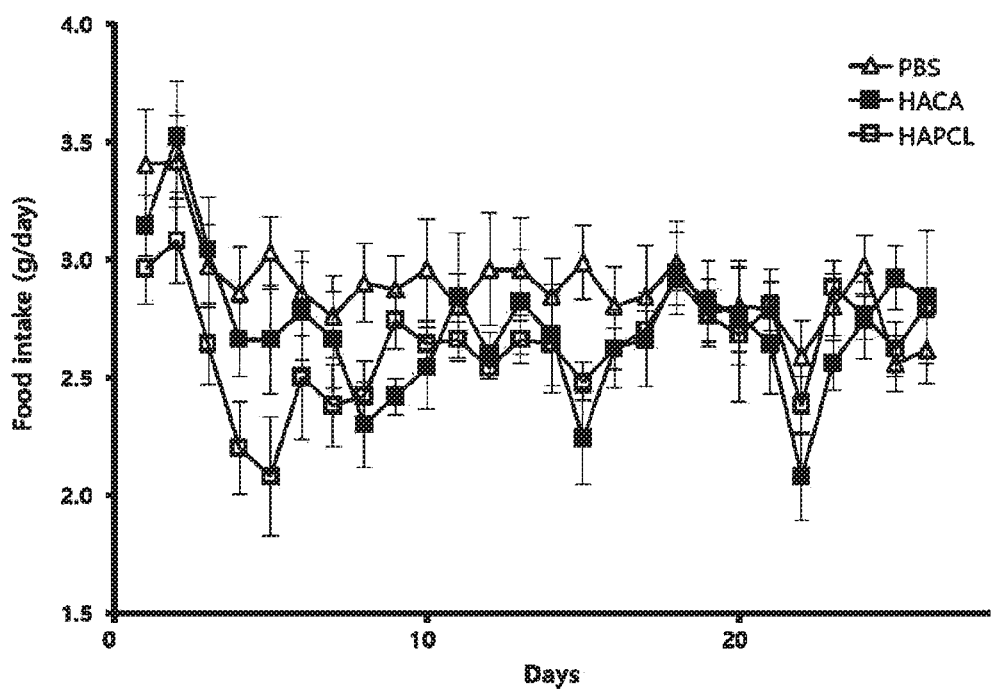
FIG. 5 illustrates the effect of hyaluronic acid nanoparticles according to an embodiment on food intake.

FIGS. 4 and 5 respectively illustrate results of analyzing changes in body weight and food intake of diabetic model mice according to administration of hyaluronic acid nanoparticles, from which it was confirmed that the group administered hyaluronic acid nanoparticles exhibited decreases in both body weight and food intake, as compared to those of the control.

1-2. Effect of Hyaluronic Acid Nanoparticles on Blood Glucose

200 µl of each of the hyaluronic acid nanoparticles HA-CA and HA-PCL was administered to diabetic model mice fed a high fat diet, at a concentration of 20 mg/kg, and then 2 g/kg of glucose was intraperitoneally (IP) injected into each mouse, and a PBS-administered group was used as a control.

Figure 6:
FIG. 6 illustrates the effect of hyaluronic acid nanoparticles according to an embodiment on blood glucose.

FIG. 6 illustrates results of observing glucose concentration in blood of diabetic model mice over time according to administration of hyaluronic acid nanoparticles, from which it was confirmed that the group administered hyaluronic acid nanoparticles exhibited improved glucose homeostasis, as compared to the control.

1-3. Insulin Resistance of Hyaluronic Acid Nanoparticles

200 µl of each of the hyaluronic acid nanoparticles HA-CA and HA-PCL was administered to diabetic model mice fed a high fat diet, at a concentration of 20 mg/kg, and then 0.5 unit/kg of insulin was intraperitoneally (IP) injected into each mouse, and a PBS-administered group was used as a control.

Figure 7:
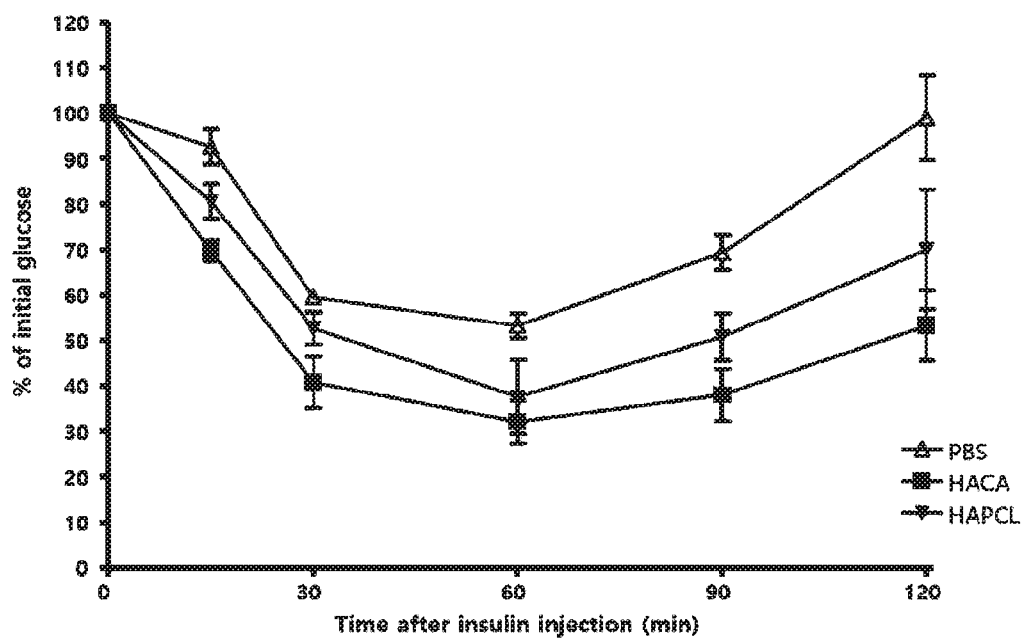
FIG. 7 illustrates insulin resistance of hyaluronic acid nanoparticles according to an embodiment.

FIG. 7 illustrates results of observing glucose concentration in blood of diabetic model mice over time according to administration of hyaluronic acid nanoparticles, from which it was confirmed that the group administered the hyaluronic acid nanoparticles exhibited improved insulin resistance, as compared to the control.

Experimental Example 2: Effect of Hyaluronic Acid Nanoparticles on High Fat Diet-Induced Inflammation

[Analysis of Gene Expression Changes]

RNA Isolation and RT-Quantitative PCR Analysis

RNA was isolated using a TRIzol reagent, and then samples with 260/280 ratio of 2.0 or greater were analyzed using Nanodrop.

Complementary DNA was synthesized using reverse transcriptase and RT-qPCR was performed with target gene-specific primers. After PCR, changes in gene expression of the experimental group and the control were analyzed by comparative quantification.

Immunohistochemistry

Slides including liver and adipose tissues of mice were immune-stained with each protein-specific antibody or hematoxylin & eosin.

2-1. Effect of Hyaluronic Acid Nanoparticles on Inflammatory Factors in Liver Tissue 200 µl of each of the hyaluronic acid nanoparticles HA-CA and HA-PCL was administered to diabetic model mice fed a high fat diet, at a concentration of 20 mg/kg, and then liver tissues were extracted, and a PBS-administered group was used as a control.

Figure 8:
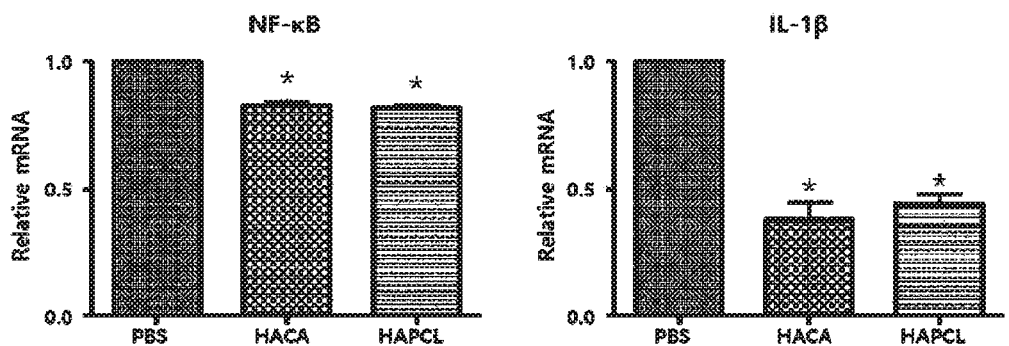
FIG. 8 illustrates the effect of hyaluronic acid nanoparticles according to an embodiment on inflammatory factors in liver tissue.

FIG. 8 illustrates results of analyzing inflammatory factors, i.e., NF-κB and IL-1β, in liver tissue according to administration of hyaluronic acid nanoparticles, from which it was confirmed that levels of inflammation-related factors were significantly reduced in the group administered the hyaluronic acid nanoparticles, as compared to those of the control.

2-2. Effect of Hyaluronic Acid Nanoparticles on Inflammatory Factors in Adipose Tissue 200 µl of each of the hyaluronic acid nanoparticles HA-CA and HA-PCL was administered to diabetic model mice fed a high fat diet, at a concentration of 20 mg/kg, and then adipose tissues were extracted, and a PBS buffer was used as a control.

Figure 9:
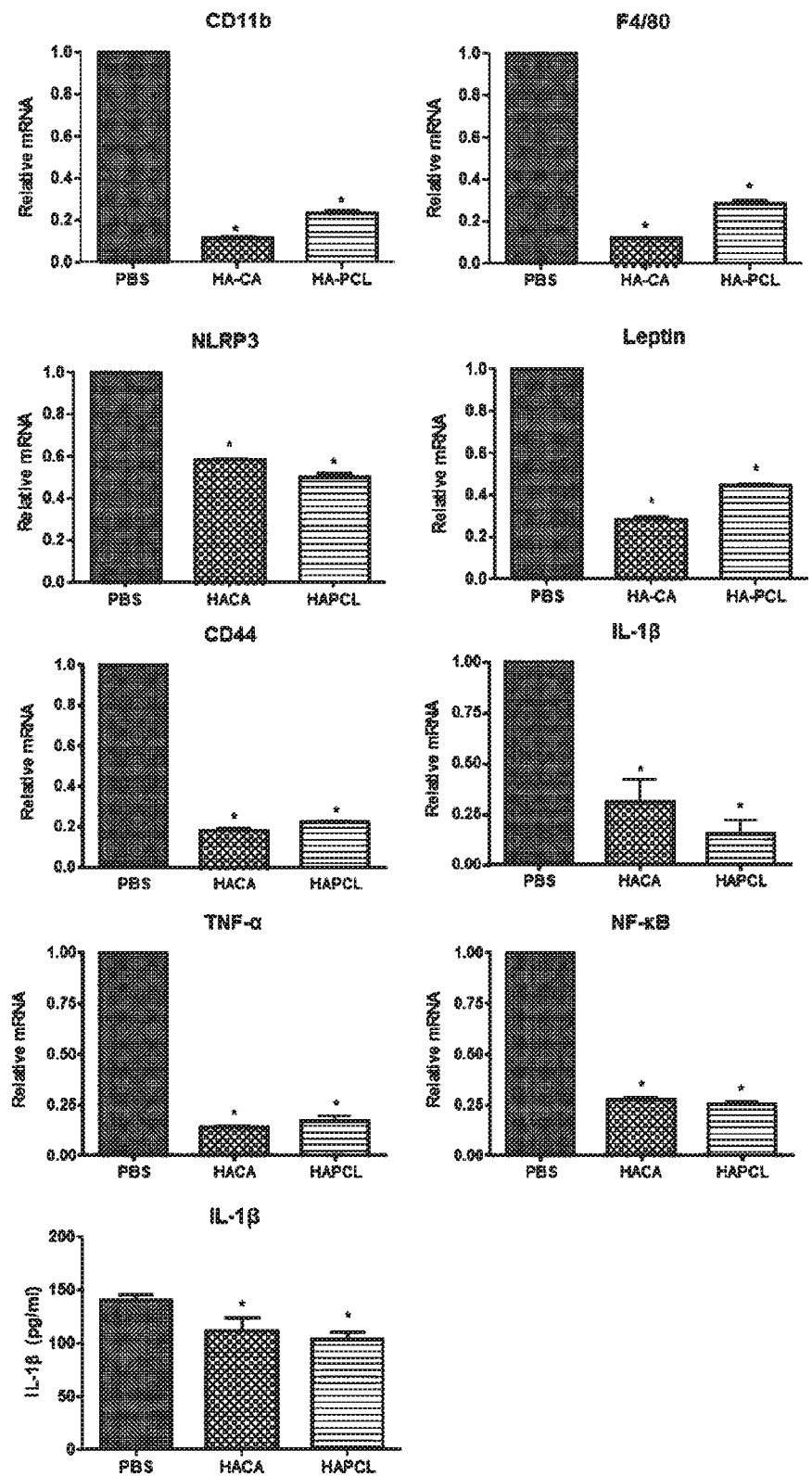
FIG. 9 illustrates the effect of hyaluronic acid nanoparticles according to an embodiment on inflammatory factors in adipose tissue.

FIG. 9 illustrates results of analyzing inflammatory factors, i.e., CD44, IL-1β, TNF-β, NF-κB, and NLRP3, in adipose tissue according to administration of hyaluronic acid nanoparticles, from which it was confirmed that expression amounts of NLRP3 inflammasome and inflammatory response inducers were significantly reduced in the group administered the hyaluronic acid nanoparticles, as compared to those of the control.

Figure 10:
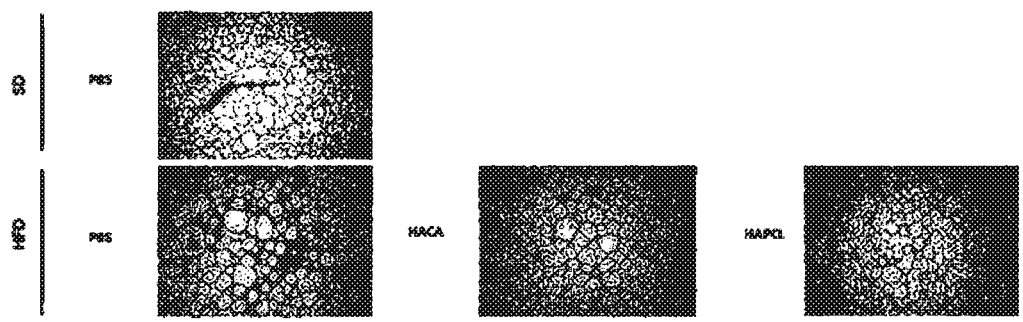
FIG. 10 is a set of SEM images showing adipose tissues stained with hematoxylin & eosin.

FIG. 10 is a set of microscope images of the extracted adipose tissues after being stained with hematoxylin & eosin, from which it was confirmed that inflammation was induced by macrophages infiltrated into the adipose tissues through high fat diet feeding and was alleviated through administration of the hyaluronic acid nanoparticles.

Figure 11:
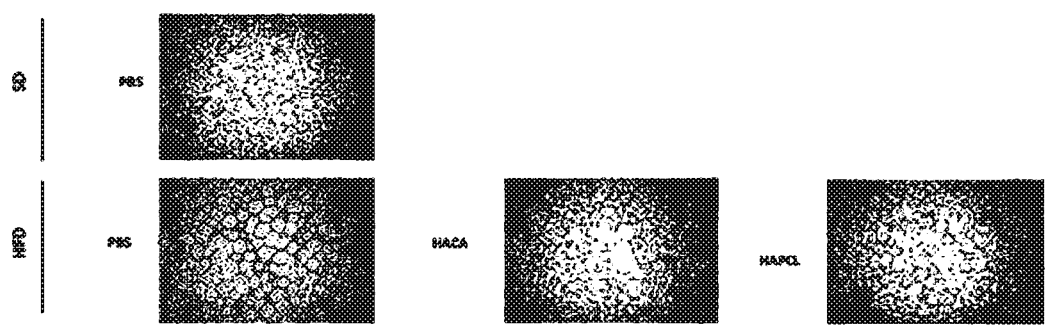
FIG. 11 is a set of SEM images showing adipose tissues immune-stained with MAC-2.

FIG. 11 illustrates microscope images of the adipose tissues stained with hematoxylin & eosin after being further immune-stained with a macrophage-specific marker MAC-2, from which it was confirmed that, as in FIG. 8, the infiltration of macrophages into adipose tissue was reduced in the experimental groups.

Experimental Example 3: Effect of Hyaluronic Acid Nanoparticles on Rheumatoid Arthritis

[Construction of Rheumatoid Arthritis (CIA-HFD) Animal Model]

3-week-old male DBA1 mice were stabilized for 1 week, and then fed a western diet (# D12079B) for 10 weeks to construct a high fat diet (HFD) model. At 7 weeks old, type II collagen (Chondrex) was subcutaneously injected into the tail of each mouse, followed by $1^{st}$ immunization and after 3 weeks, $2^{nd}$ boosting was performed to thereby induce arthritis. Subsequently, 20 mg/kg of a vehicle or HA-CA of Example 1 was intravenously administered to each group for 4 weeks.

3-1. Effect of Hyaluronic Acid Nanoparticles on Symptoms and Incidence of Rheumatoid Arthritis After $2^{nd}$ boosting, the experimental rheumatoid arthritis (collagen induced arthritis (CIA)) model underwent swelling of the limbs and ankle joints. Such degrees of swelling were scored to analyze the progression of arthritis. The drug was administered for 4 weeks, and the degree of swelling of the ankle of each mouse was measured once every two days to evaluate the progression of arthritis. To increase measurement reliability, the measurement was performed three times. In addition, individuals with a specific score or higher (score #2) were defined as individuals with arthritis, and it was analyzed how fast or how much the number of individuals with arthritis increased.

For specific scoring criteria, refer to the published paper (Inglis J J et al., protocol for the induction of arthritis in C57BL/6 mice. Nat Protoc 2008; 3:612-8), and scoring may be made between 0 and 4. 0 indicates no abnormality, 1 indicates a slightly swollen state or a steadily tightened state of mouse's feet, 2 indicates a state in which one toe was distinctly swollen in red or distinctly swollen but not severe, 3 indicates a state in which one toe was distinctly swollen in red and dorsum of foot was distinctly swollen, but not severe, or two or more toes were distinctly swollen, and 4 indicates a state in which all feet were swollen and turned red.

Figure 12:
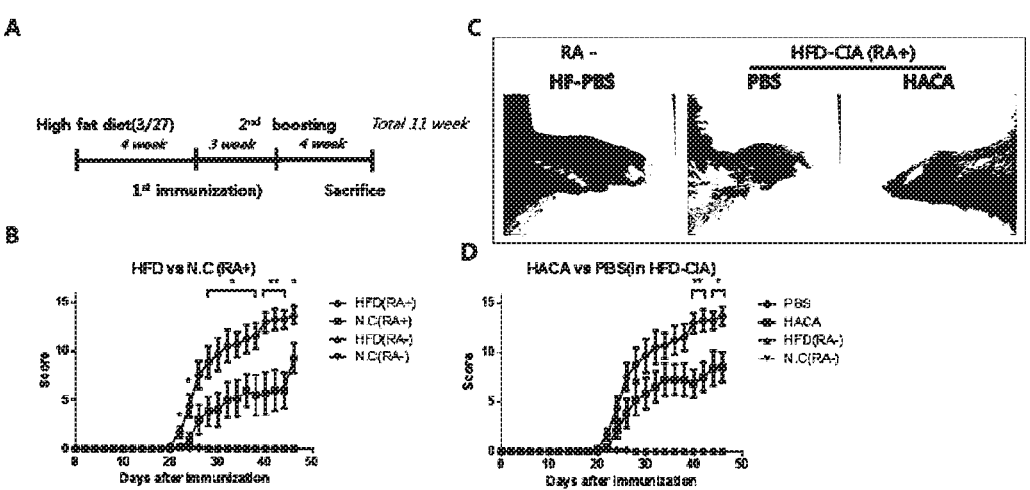
FIG. 12 illustrates the effect of hyaluronic acid nanoparticles on alleviating rheumatoid arthritis in a rheumatoid arthritis animal model.
Figure 13:
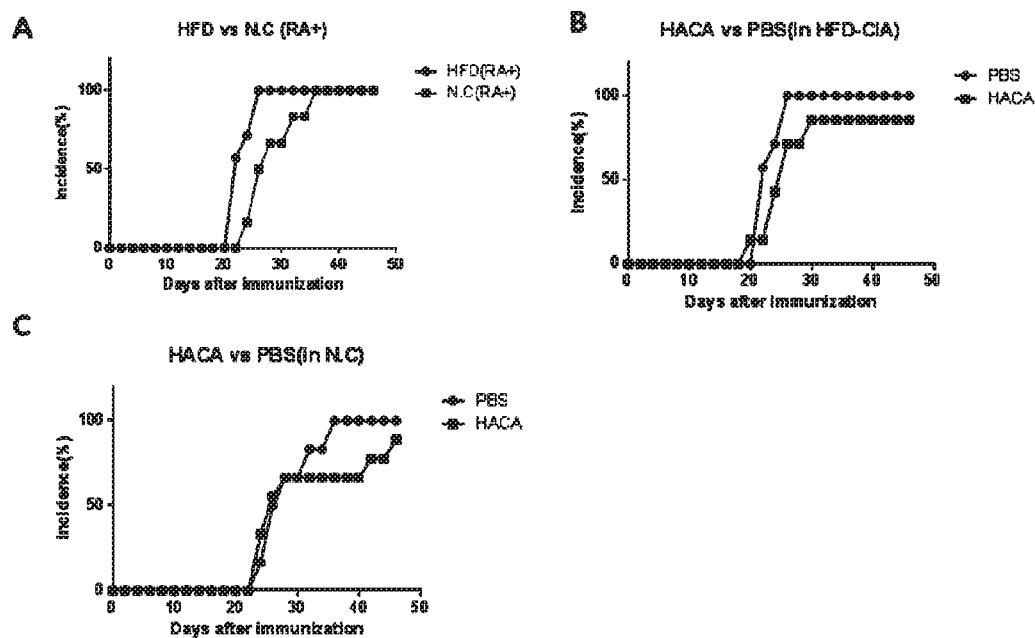
FIG. 13 illustrates the effect of hyaluronic acid nanoparticles on inhibiting the incidence of rheumatoid arthritis.

FIGS. 12 and 13 illustrate the effect of hyaluronic acid nanoparticles on symptoms and incidence of rheumatoid arthritis using a rheumatoid arthritis animal model, from which it was confirmed that the symptoms and incidence of rheumatoid arthritis worsened by a high fat diet were reduced in the group administered the hyaluronic acid nanoparticles.

3-2. Effect of Hyaluronic Acid Nanoparticles on Degree of Joint Tissue Destruction in Rheumatoid Arthritis Animal Model The extracted tissues (ankle and knee) were fixed, embedded, and then sectioned to prepare paraffin sections. The sections were stained with Mayer's Hematoxylin, Fast green, and Safranin O solution, and the degrees of destruction of immune cells infiltrated into joint tissue synovium or bone, and joints were analyzed.

Figure 14:
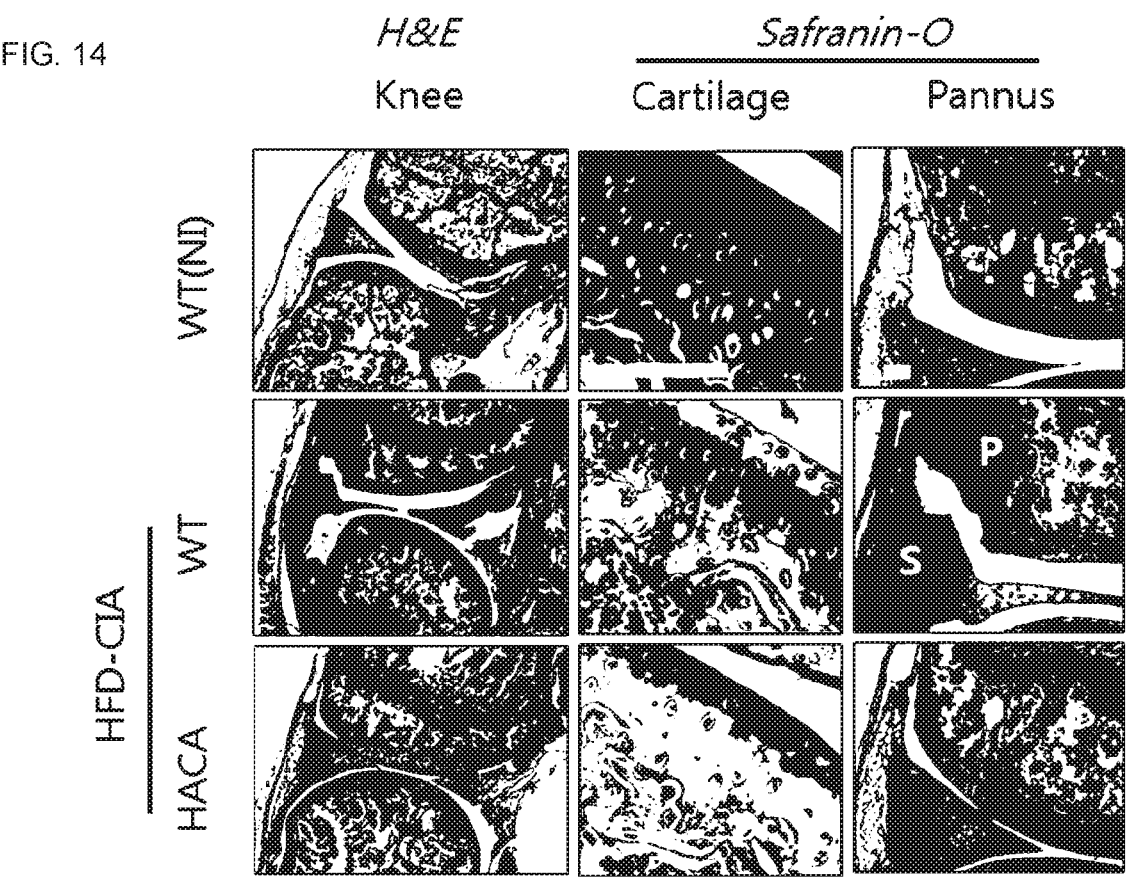
FIG. 14 is a set of images of knee and ankle joint tissues stained with Safranin O.

Referring to FIG. 14, it was confirmed that cartilage destruction, synovitis, and bone erosion, which occur in rheumatoid arthritis, were alleviated in the group administered the hyaluronic acid nanoparticles.

Experimental Example 4: Effect of Hyaluronic Acid Nanoparticles on Degenerative Arthritis

[Chondrocyte Culture and Confirmation of Inhibition of Joint Inflammation and Cartilage Destruction by Hyaluronic Acid Nanoparticles]

Chondrocytes were obtained from the cartilage tissue derived from femoral heads, femoral condyles, and tibial plateaus of normal mice at an age of 5 days after birth. The obtained chondrocytes were cultured in DMEM (Gibco, USA) containing 10% (v/v) fetal bovine serum (Gibco, USA), 50 µg/ml of streptomycin (Sigma-Aldrich, USA), and 50 unit/ml of penicillin (Sigma-Aldrich, USA) in a cell incubator under conditions of 37° C. and 5% $CO_2$.

IL-1β is a typical inflammatory cytokine that promotes joint inflammation and cartilage tissue destruction. The chondrocytes were treated with 5 ng/ml of IL-1β according to time, and then qRT-PCR was performed on Mmp3, Mmp13, Cox2, IL-6, and GAPDH using conditions and primers shown in Table 1 below.

TABLE 1

| SEQ ID NO. | Sequence (5'-3') | sense/ antisense | gene | size (bp) | Annealing temperature (AT, °C.) |
|---|---|---|---|---|---|
| 1 | TCCTGATGTTGGTGGCTTCAG | S | Mmp3 | 102 | 58 |
| 2 | TGTCTTGGCAAATCCGGTGTA | AS | | | |
| 3 | TGATGGACCTTCTGGTCTTCTGG | S | Mmp13 | 473 | 55 |
| 4 | CATCCACATGGTTGGGAAGTTCT | AS | | | |
| 5 | GGTCTGGTGCCTGGTCTGATGAT | S | Cox2 | 724 | 65 |
| 6 | GTCCTTTCAAGGAGAATGGTGC | AS | | | |
| 7 | ACCACTCCCAACAGACCTGTCTATACC | S | IL-6 | 435 | 60 |
| 8 | CTCCTTCTGTGACTCCAGCTTATCTGTTAG | AS | | | |
| 9 | TCACTGCCACCCAGAAGAC | S | GAPDH | 450 | 55 |
| 10 | TGTAGGCCATGAGGTCCAC | AS | | | |

Figure 15:
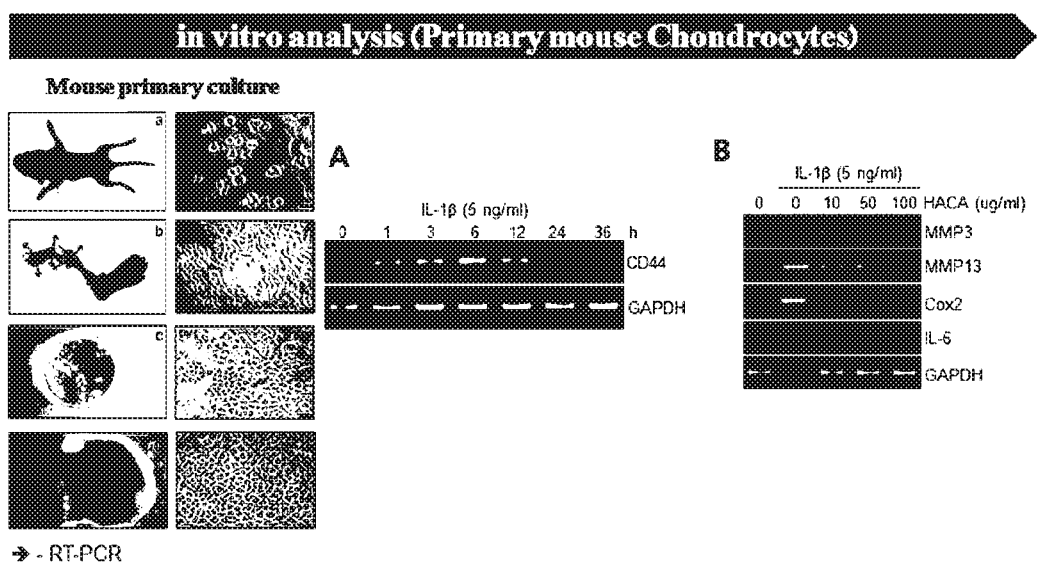
FIG. 15 illustrates results of confirming that joint inflammation and cartilage tissue destruction could be alleviated and inhibited by hyaluronic acid nanoparticles in degenerative arthritis.

Referring to FIG. 15, it was confirmed that the expression of Mmp3, Mmp13, Cox2, and IL-6, which was increased by IL-1β in the chondrocytes, was reduced by the hyaluronic acid nanoparticles in a concentration-dependent manner. This indicates that joint inflammation and cartilage tissue destruction may be alleviated and inhibited by hyaluronic acid nanoparticles.

INDUSTRIAL APPLICABILITY

A pharmaceutical composition for preventing or treating an inflammatory disease or a metabolic disease, which includes hyaluronic acid nanoparticles, according to the present invention reduces body weight, lowers food intake, has an effect of reducing blood glucose as a result of a glucose tolerance test (GTT), and has an effect of reducing insulin resistance, inflammatory inducers (NF-κB, IL-1β, CD44, TNF-α, NLRP3 inflammasome, and the like), and macrophage tissue infiltration, and thus may be effectively used as a pharmaceutical composition for preventing or treating inflammatory diseases or metabolic diseases.

Sequence List Free Text

Electronic file attached.

---

The invention claimed is:

1. A method for treating an inflammatory disease or a metabolic disease, the method comprising administering an effective amount of hyaluronic acid nanoparticles represented by Formula (1) or (2) below:

[Formula 1]

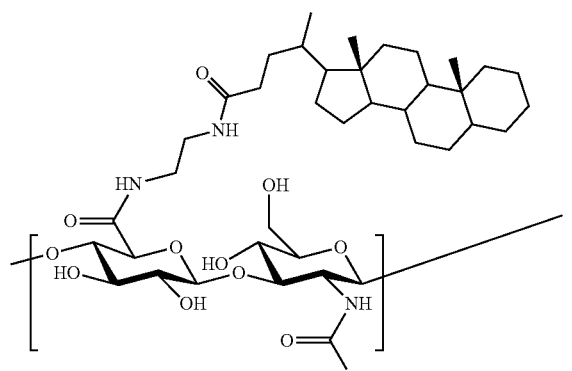

[Formula 2]

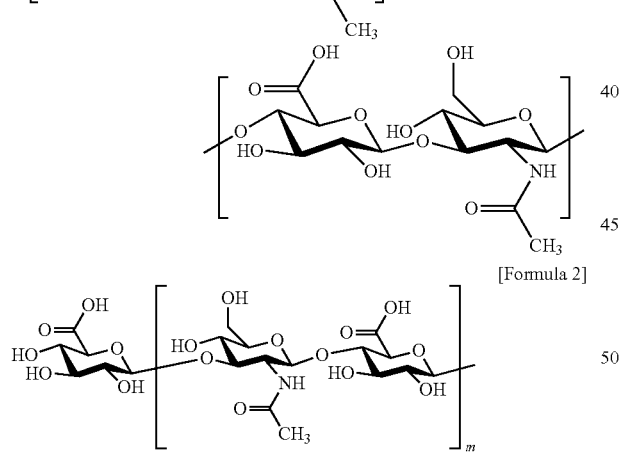

-continued

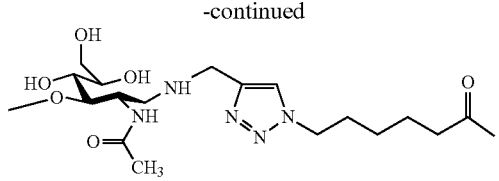

wherein the hyaluronic acid nanoparticles of Formula (1) consists of hyaluronic acid and 5β-cholanic acid in a mass ratio of 1:0.05 to 1:0.3, wherein the hyaluronic acid nanoparticles of Formula (2) consists of hyaluronic acid and polycaprolactone in a mass ratio of 1:0.2 to 1:0.4, wherein the hyaluronic acid nanoparticles have a diameter of 207.5 nm to 224 nm, wherein the inflammatory disease is selected from the group consisting of arthritis, rhinitis, hepatitis, keratitis, gastritis, enteritis, nephritis, bronchitis, pleurisy, peritonitis, spondylitis, pancreatitis, inflammatory pain, urethritis, cystitis, burn inflammation, dermatitis, periodontitis, gingivitis, and degenerative nerve inflammation, and wherein the metabolic disease is type 2 diabetes or obesity.

2. The method according to claim 1, wherein the hyaluronic acid nanoparticles are formed through self-assembly in an aqueous solution.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Mmp3 primer sense

<400> SEQUENCE: 1
tcctgatgtt ggtggcttca g                                    21

<210> SEQ ID NO 2
<211> LENGTH: 21
<212> TYPE: DNA
<213> ORGANISM: Artificial Sequence
<220> FEATURE:
<223> OTHER INFORMATION: Mmp3 primer antisense

<400> SEQUENCE: 2
tgtcttggca aatccggtgt a                                    21

<210> SEQ ID NO 3
<211> LENGTH: 23

```
<212> TYPE: DNA
<213> ORGANISM: Artificial Sequence
<220> FEATURE:
<223> OTHER INFORMATION: Mmp13 primer sense

<400> SEQUENCE: 3
tgatggacct tctggtcttc tgg                                             23

<210> SEQ ID NO 4
<211> LENGTH: 23
<212> TYPE: DNA
<213> ORGANISM: Artificial Sequence
<220> FEATURE:
<223> OTHER INFORMATION: Mmp13 primer antisense

<400> SEQUENCE: 4
catccacatg gttgggaagt tct                                             23

<210> SEQ ID NO 5
<211> LENGTH: 23
<212> TYPE: DNA
<213> ORGANISM: Artificial Sequence
<220> FEATURE:
<223> OTHER INFORMATION: Cox2 primer sense

<400> SEQUENCE: 5
ggtctggtgc ctggtctgat gat                                             23

<210> SEQ ID NO 6
<211> LENGTH: 22
<212> TYPE: DNA
<213> ORGANISM: Artificial Sequence
<220> FEATURE:
<223> OTHER INFORMATION: Cox2 primer antisense

<400> SEQUENCE: 6
gtcctttcaa ggagaatggt gc                                              22

<210> SEQ ID NO 7
<211> LENGTH: 27
<212> TYPE: DNA
<213> ORGANISM: Artificial Sequence
<220> FEATURE:
<223> OTHER INFORMATION: IL-6 primer sense

<400> SEQUENCE: 7
accactccca acagacctgt ctatacc                                         27

<210> SEQ ID NO 8
<211> LENGTH: 30
<212> TYPE: DNA
<213> ORGANISM: Artificial Sequence
<220> FEATURE:
<223> OTHER INFORMATION: IL-6 primer antisense

<400> SEQUENCE: 8
ctccttctgt gactccagct tatctgttag                                      30

<210> SEQ ID NO 9
<211> LENGTH: 19
<212> TYPE: DNA
<213> ORGANISM: Artificial Sequence
<220> FEATURE:
<223> OTHER INFORMATION: GAPDH primer sense

<400> SEQUENCE: 9
```

```
tcactgccac ccagaagac                                                    19

<210> SEQ ID NO 10
<211> LENGTH: 19
<212> TYPE: DNA
<213> ORGANISM: Artificial Sequence
<220> FEATURE:
<223> OTHER INFORMATION: GAPDH primer antisense

<400> SEQUENCE: 10
tgtaggccat gaggtccac                                                    19
```